United States Patent [19]

Gennari

[11] Patent Number: 4,558,122

[45] Date of Patent: Dec. 10, 1985

[54] STABLE S-ADENOSYLMETHIONINE DERIVATIVES, THE PROCESS FOR THEIR PREPARATION, AND THERAPEUTIC COMPOSITIONS WHICH CONTAIN THEM AS ACTIVE PRINCIPLE

[75] Inventor: Federico Gennari, Truccazzano, Italy

[73] Assignee: Bioresearch S.P.A., Milan, Italy

[21] Appl. No.: 414,044

[22] Filed: Sep. 2, 1982

[30] Foreign Application Priority Data

Sep. 11, 1981 [IT] Italy ............................. 23940 A/81

[51] Int. Cl.⁴ ...................... C07H 15/12; C07H 17/00
[52] U.S. Cl. .................................................... 536/26
[58] Field of Search ........................................... 536/26

[56] References Cited

U.S. PATENT DOCUMENTS

| | | | |
|---|---|---|---|
| 2,969,353 | 1/1961 | Shunk et al. | 536/26 |
| 3,707,536 | 12/1972 | Haid et al. | 536/26 |
| 3,893,999 | 7/1975 | Fiecchi | 536/26 |
| 3,954,726 | 5/1976 | Fiecchi | 536/26 |
| 4,057,686 | 11/1977 | Fiecchi | 536/26 |
| 4,242,505 | 12/1980 | Kawahara et al. | 536/26 |

FOREIGN PATENT DOCUMENTS

| | | | |
|---|---|---|---|
| 2275220 | 2/1976 | France | 536/26 |
| 0160294 | 12/1975 | Japan | 536/26 |
| 0099499 | 8/1981 | Japan | 536/26 |
| 0145299 | 11/1981 | Japan | 536/26 |
| 0156500 | 9/1982 | Japan | 536/26 |

*Primary Examiner*—Ethel G. Love
*Attorney, Agent, or Firm*—Stevens, Davis, Miller & Mosher

[57] ABSTRACT

New S-adenosylmethionine (SAM) salts of formula

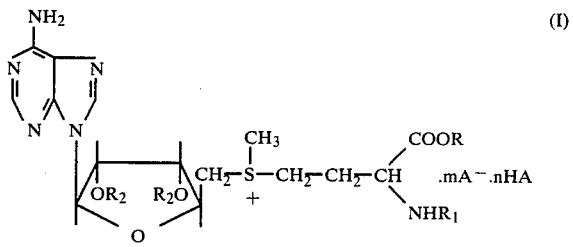

have been prepared in which R, $R_1$, $R_2$, m, n and A are as defined in the text.

The methods of preparing the new products starting from SAM salts are described.

The new products are stable and highly bioavailable, particularly when administered orally.

10 Claims, No Drawings

STABLE S-ADENOSYLMETHIONINE DERIVATIVES, THE PROCESS FOR THEIR PREPARATION, AND THERAPEUTIC COMPOSITIONS WHICH CONTAIN THEM AS ACTIVE PRINCIPLE

This invention relates to a new class of S-adenosylmethionine (SAM) derivatives of formula

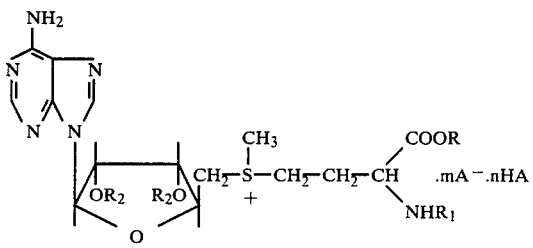

in which R is H, or a linear or branched aliphatic radical of 1-6 carbon atoms; $R_1$ is H, or a linear or branched aliphatic or aromatic acyl of 2-12 carbon atoms; $R_2$ is H, or a linear or branched aliphatic or aromatic acyl of 2-12 carbon atoms; m is 0 or 1; n is 0-5; and A is the equivalent of an inorganic or organic acid of pK less than 2.5, in which $R_1$ can be the same as or different from $R_2$, and at least one of the radicals R, $R_1$, $R_2$ is other than hydrogen.

SAM is known to be a substance present in all living organisms, which participates in a great number of biological processes of fundamental importance in that it represents the major donor of methyl groups in the organism.

It is also known that up to 1975 any practical application of SAM was prevented by its extreme instability.

From 1975 onwards, the applicant filed a series of patents (U.S. Pat. Nos. 3,893,999, 3,954,726, 4,057,686) relative to particular SAM salts which, completely unexpectedly, have demonstrated stability characteristics such as to allow the preparation of pharmaceutical formulations useful in numerous fields of human therapy.

Although solving one of the negative aspects of SAM, these salts have however still not solved the other problem connected with this product, namely its low capacity for passing through cell barriers, with consequent difficulty of absorption by the organism, particularly when administered orally.

A new class of products, namely the products of formula (I) has now been found, and forms the subject matter of the present invention, which completely unexpectedly possesses all the pharmacological activity already determined for SAM salts, and also possesses equal or greater stability, even at elevated temperatures, and greater bioavailability.

In particular, this latter characteristic makes it possible to prepare pharmaceutical formulations for oral use, which are very useful in human therapy.

Among the compounds of formula (I) which are of particular interest are the esters of formula

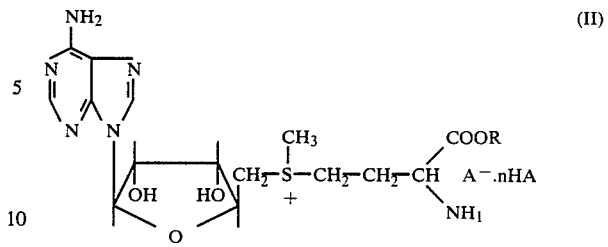

in which R is a linear or branched aliphatic radical of 1 to 6 carbon atoms, $A^-$ is an equivalent of a generic anion of a strong inorganic or organic acid characterised by a pK of less than 2.5, m is 1, and n can vary from 0 to 4, but is preferably 3, and acylated derivatives of formula:

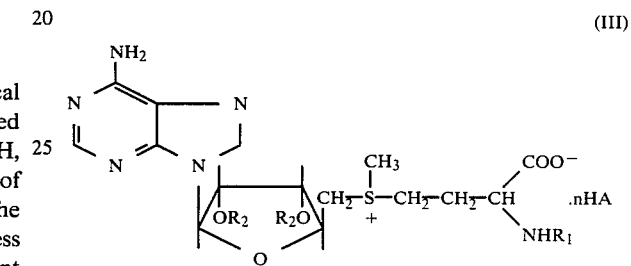

in which $R_1$, which can be the same as or different from $R_2$, is a linear or branched aliphatic or aromatic acyl containing 2 to 12 carbon atoms; A is an equivalent of an inorganic or organic acid of pK <2.5, m is 0, and n can vary from 1 to 5 but is preferably 4.

It has also been found that the stability of the new compounds (I) is substantially influenced by the number of acid equivalents bonded to each molecule. In particular, for compounds of formula (II), maximum stability is obtained when n=3, whereas for compounds of formula (III) maximum stability is obtained when n=4.

The stability data of some of the new products are given in the following tables. More specifically, Table 1 shows data relative to the stability, compared with SAM, of certain esters of formula (II) in aqueous solution at 100° C., for various pH values, all with n=3.

TABLE 1

| R | pH of solution | Temperature | % decomposition after | | | |
|---|---|---|---|---|---|---|
| | | | 15 min | 30 min | 60 min | 240 min |
| H | 2 | 100° C. | 80 | 100 | 100 | 100 |
| H | 3 | 100° C. | 90 | 100 | 100 | 100 |
| H | 4 | 100° C. | 100 | 100 | 100 | 100 |
| $CH_3$ | 2 | 100° C. | 5 | 10 | 21 | 75 |
| $CH_3$ | 3 | 100° C. | 6 | 13 | 25 | 100 |
| $CH_3$ | 4 | 100° C. | 8 | 18 | 40 | 100 |
| $C_2H_5$ | 2 | 100° C. | 2 | 4 | 8 | 35 |
| $C_2H_5$ | 3 | 100° C. | 3 | 6 | 13 | 55 |
| $C_2H_5$ | 4 | 100° C. | 5 | 9 | 19 | 80 |
| $C_4H_9$ | 2 | 100° C. | 2 | 4 | 8 | 30 |
| $C_4H_9$ | 3 | 100° C. | 3 | 6 | 12 | 52 |
| $C_4H_9$ | 4 | 100° C. | 4 | 9 | 17 | 75 |

The acyl derivatives of formula (III) have shown poor stability in solution, so that under these conditions the esters are certainly to be considered superior.

Table 2 shows the stability in the dry state, at 45° C., of certain SAM acyl derivatives of formula (III) in comparison with SAM

TABLE 2

| Product | Degradation at 45° C. after | | | | |
|---|---|---|---|---|---|
| | 60 days | 120 days | 180 days | 240 days | 360 days |
| SAM. $H_2SO_4$ | 80% | 100% | 100% | 100% | 100% |
| SAM monoacetyl. 2 $H_2SO_4$ ($R_2$=H) | 0 | 1.4% | 3% | 4.6% | 5.5% |
| SAM triacetyl. 2 $H_2SO_4$ | 1% | 1.9% | 4.1% | 5.9% | 8% |

The esters of formula (II) are stable indefinitely in the dry state at 45° C.

As initially stated, a further extremely advantageous aspect of the new products of formula (I) derives from their capacity for passing through cell barriers.

The values given in Table 3 below indicate this characteristic of the new products.

In the 1st test, known as "in situ" (intestinal sacs), 2 mg of each product to be tested in 1 ml of physiological solution were placed in intestinal sacs provided in rats under ether anesthesia. The rats were killed after 2 hours, and the residual content of the sac (wall+content) was analysed.

In the 2nd test, portions of intestine turned inside out were used, incubated at 37° C. in accordance with Krebs Ringer against an external product concentration of $10^{-4}$ M. The products were all salified with $H_2SO_4$ to give salts in which m was 0 or 1 and n was 3.

TABLE 3

| Product tested | | | PRODUCT ABSORPTION | |
|---|---|---|---|---|
| | | | in sacs | intestine inside out |
| R | $R_1$ | $R_2$ | % of dose | nmoles/h/mg tissue |
| H | H | H | 5 | 0.009 |
| $CH_3$ | H | H | 55 | 0.078 |
| $C_2H_5$ | H | H | 59 | 0.061 |
| $C_3H_7$ | H | H | 61 | 0.045 |
| $C_4H_9$ | H | H | 65 | 0.037 |
| $C_5H_{11}$ | H | H | 68 | 0.025 |
| $C_6H_{13}$ | H | H | 67 | 0.023 |
| H | $COCH_3$ | H | 10 | 0.046 |
| H | $COC_4H_9$ | H | 18 | 0.028 |
| H | $COC_6H_5$ | H | 12 | 0.017 |
| H | p.tol. sulphon. | H | 13 | 0.021 |
| H | Succinyl | H | 25 | 0.016 |
| H | Glutaryl | H | 23 | 0.018 |
| H | Octyl | H | 62 | 0.023 |
| H | Dodecyl | H | 65 | 0.019 |
| H | $COCH_3$ | $COCH_3$ | 65 | 0.047 |
| H | $COC_4H_9$ | $COC_4H_9$ | 87 | 0.031 |
| H | Succinyl | $COCH_3$ | 91 | 0.035 |

The new products of formula (I) were prepared by the processes specified hereinafter.

(A) SAM esters of formula (II)

The new SAM esters can be prepared from any SAM salt prepared by known methods. The sulphate is preferably used.

A solution is prepared having a concentration between 1% and 3% (preferably 2%) of concentrated sulphuric acid in the anhydrous alcohol with which it is intended to esterify the SAM.

A sufficient quantity of SAM sulphate is added under stirring to this solution, to obtain a final concentration of SAM ions of between 10 and 100 g/l, and preferably 50.

A clear solution is obtained with low molecular weight alcohols, whereas a suspension is obtained with high molecular weight alcohols.

It is heated under reflux for 10-20 hours according to the alcohol used. At the end of the reaction, a clear solution is obtained in all cases.

Besides the SAM ester, the final reaction mixture contains small residual quantities of SAM (up to a maximum of 5%) and SAM thermal degradation products of a quantity variable according to the alcohol used.

The proportions range from 80% of ester conversion and 20% of degradation products in the case of methyl ester, to 50% conversion and 50% degradation in the case of $C_5-C_6$ alcohols.

The reaction mixture is cooled, and an equal volume of $H_2O$ is added (or it is extracted with $H_2O$ if the alcohol is immiscible with $H_2O$).

The excess sulphuric acid is removed by adjusting the pH to 3 by the addition of a basic resin of $OH^-$ form (AMBERLITE IRA 401 or AMBERLITE IRA 93).

The resin is filtered and sent for regeneration.

In the case of alcohols miscible with $H_2O$, the alcohol is evaporated under vacuum.

If the residual SAM in the solution obtained in this manner exceeds 1%, the solution is boiled for 20 minutes in order to destroy the residual SAM.

The pH is adjusted under stirring to 6.5, and the solution is passed through a column of weak acid resin of $H^+$ form (AMBERLITE IRC 50 or CG 50) which has previously been washed with $H_2O$, while respecting the following column operation parameters:
ratio of diameter/height of resin bed 1:10;
charge 20 g of SAM ester/liter of resin;
flow 1 column volume/hour.

The column is then washed with 1 column volume of $H_2O$ and 0.1N acetic acid until the pH of the eluate is 3.

It is washed with a further volume of water.

The SAM ester is eluted with 0.1N $H_2SO_4$ (or with another strong acid if a different salt is required).

The solution thus obtained is concentrated under vacuum to 50 g/l.

It is filtered with activated charcoal (1/10 of the SAM ester), the acid composition is adjusted to the required value (3 to 5 equivalents, preferably 4) by adding concentrated $H_2SO_4$ (or another strong acid), and the solution is lyophilised.

(B) SAM acyl derivatives of formula (III)

The raw material is again any soluble SAM salt, preferably the sulphate.

A solution of SAM salt in $H_2O$ is prepared in such a manner that the SAM concentration lies between 50 and 200 g/l, preferably 100.

The solution is cooled to 1° C., and while keeping this temperature constant by cooling. The pH is adjusted to 7 using 2N NaOH.

The procedure is as follows, according to the derivative which it is required to obtain.
Monoacyl derivatives of $C_2-C_6$ aliphatic acids and aromatic acids.

The acylating agent (anhydride or chloride of the required acid, at choice) is added in small portions in the molar proportion of 1:1.2 relative to the SAM, while keeping the temperature at 1° C. and the pH at 7 by the addition of 2N NaOH.

At the end of the reaction (i.e. when the pH remains stable) the temperature is allowed to rise to 20° C.

The solution is diluted to a concentration of 20 g/l, and any precipitate is filtered off.

The conversion of the SAM to the monoacyl derivative is greater than 90%.

The solution thus obtained is chromatographed over ion exchange resin.

Monoacyl derivatives of $C_7$–$C_{12}$ aliphatic acids.

The chloride of the required acid is dissolved, in a molar quantity of 1:3 relative to the SAM, in an anhydrous solvent (acetone, DMFA, DMSO or the like) to obtain a 10% solution, and this is added in small portions while maintaining the temperature at 1° C. and the pH at 7 by the addition of 2N NaOH.

At the end of the reaction, the temperature is allowed to rise to 20° C.

The solution is diluted to a concentration of 20 g/l, the solvent is evaporated under vacuum, and the precipitate is filtered off.

The conversion to the monoacyl derivative is about 80% in this case.

The solution thus obtained is chromatographed over ion exchange resin.

Triacyl derivatives of $C_2$–$C_6$ aliphatic and mixed acids. The acylating agent is added in a molar quantity of between 1:5 and 1:10 relative to the SAM, while always maintaining the temperature at 1° C. and the pH at 7 by the addition of 2N NaOH.

At the end of the reaction, the temperature is allowed to rise to 20° C.

The conversion of the SAM to the triacyl derivative is about 80%.

The solution is diluted to a concentration of 20 g/l, and any precipitate is filtered off.

The solution thus obtained is chromatographed over ion exchange resin.

In all the cases previously considered, a column of weak acid resin (AMBERLITE IRC 50 or CG 50) in H+ form previously washed with $H_2O$ is used, while respecting the following operating parameters:
ratio of diameter/height of resin bed 1:10
charge 20 g of SAM derivative/liter of resin
flow 1 column volume/hour.

The column is then washed with 1 volume of $H_2O$ and 0.1N acetic acid until the pH of the eluate is 3. It is washed with 20 mN $H_2SO_4$ until complete elution of the residual SAM and other by-products, and the required product is eluted with 0.1N $H_2SO_4$ (or with another strong acid if a different salt is required).

The solution thus obtained is concentrated under vacuum to 50 g/l.

It is filtered with activated charcoal (1/10 of the SAM derivative), the acid composition is adjusted to the required stoichiometric value, and the solution is lyophilised.

(C) Mixed derivatives of formula (I)

SAM derivatives in which R, $R_1$ and $R_2$ are all other than hydrogen, are prepared by firstly esterifying as described under paragraph (A), and then subjecting the obtained esters to acylation in aqueous solution, as described under paragraph (B).

Some non-limiting examples of preparation of SAM derivatives are described hereinafter in order to illustrate the present invention.

EXAMPLE 1

A quantity of SAM sulphate equal to 1 kg of SAM ions is dissolved in 20 l of methanol containing 2% by volume of concentrated sulphuric acid. The solution is heated under reflux for 16 hours. It is cooled and diluted with 20 l of distilled $H_2O$.

It is treated with AMBERLITE IRA 93 resin (previously activated with 2N NaOH and washed until neutral) until the pH is 3. About 15 l of resin are used.

The mixture is filtered and washed with distilled water. The methanol is evaporated under vacuum. The solution is boiled for 20 minutes in order to remove the last traces of unreacted SAM, and then cooled.

A column of AMBERLITE IRC 50 resin in H+ form is prepared containing 40 l of resin activated with 100 l of 0.5N $H_2SO_4$ washed until neutral. The previously obtained solution is neutralised to pH 6.5 with 2N NaOH, and is passed through the column at a rate of 40 l/h. This is washed with 40 l of $H_2O$.

A 0.1N acetic acid solution is passed through the column until the eluate has a pH of 3 (about 200 l), followed by 40 l of distilled water.

It is eluted with 60 l of 0.1N $H_2SO_4$. The eluate is concentrated under vacuum (35° C., 30 mmHg) to about 10 liters, 50 g of activated charcoal are added, and the mixture filtered. The solution is titrated.

A sufficient quantity of concentrated sulphuric acid is added to attain a SAM methyl ester:sulphuric acid molar ratio of 1:2, and the solution is then lyophilised.

820 g of product is obtained, of composition:
SAM methyl ester: 66.8%
$H_2SO_4$: 31.7%
$H_2O$: 1.5%
equal to a yield of 54.7% with respect to the SAM ion.

When analysed by HPLC (PARTISIL 10 SCX column, eluent AMMONIUM FORMATE 0.1M pH 4, 20% methanol, flow 1 ml/min.) the product shows a single peak with a retention time of 580 seconds.

The product was identified by U.V. and NMR spectra.

U.V. spectrum: At pH 4, absorption maximum at 258 nm with $\epsilon=14,040$, At pH 1, absorption maximum at 256 nm with $\epsilon=13,500$.

NMR spectrum: At 3 p.p.m., singlet of the S+—CH$_3$ group At 3.7 p.p.m., singlet of the

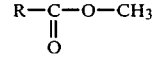

group.

If the stoichiometric composition is adjusted before lyophilisation to a SAM methyl ester:sulphuric acid ratio of 1:1.5 or 1:2.5 and the solution then lyophilised, the following respective salts are obtained:
SAM methyl ester.1.5 $H_2SO_4$.0.5$H_2O$
SAM methyl ester.2.5 $H_2SO_4$.0.5$H_2O$ If the IRC 50 column is eluted with hydrochloric acid instead of sulphuric acid, the following salts are obtained:
SAM methyl ester.3HCl.0.5$H_2O$
SAM methyl ester.4HCl.0.5$H_2O$
SAM methyl ester.5HCl.0.5$H_2O$.

Likewise, by using methane sulphonic acid, the corresponding methane sulphonates are obtained.

The analytical data for these salts are given in the following table.

| Salt | Empirical Formula | % N Calc. | % N Found | % S Calc. | % S Found | $E_{1\% \ 1 \ cm}$ pH = 4 |
| --- | --- | --- | --- | --- | --- | --- |
| Methyl ester.1.5 $H_2SO_4.0.5H_2O$ | $C_{16}H_{27}N_6O_{11}S_{2.5}.0.5H_2O$ | 14.79 | 14.78 | 14.08 | 14.01 | 247 |
| Methyl ester.2 $H_2SO_4.0.5H_2O$ | $C_{16}H_{28}N_6O_{13}S_3.0.5H_2O$ | 13.61 | 13.73 | 15.56 | 15.61 | 228 |
| Methyl ester.2.5 $H_2SO_4.0.5H_2O$ | $C_{16}H_{29}N_6O_{15}S_{3.5}.0.5H_2O$ | 12.61 | 12.59 | 16.82 | 16.72 | 211 |
| Methyl ester.3 $HCl.0.5H_2O$ | $C_{16}H_{27}N_6O_5SCl_3.0.5H_2O$ | 15.85 | 15.79 | 6.04 | 6.01 | 265 |
| Methyl ester.4 $HCl.0.5H_2O$ | $C_{16}H_{28}N_6O_5SCl_4.0.5H_2O$ | 14.81 | 14.87 | 5.64 | 5.65 | 248 |
| Methyl ester.5 $HCl.0.5H_2O$ | $C_{16}H_{29}N_6O_5SCl_5.0.5H_2O$ | 13.93 | 13.95 | 5.31 | 5.29 | 233 |
| Methyl ester.3 $CH_3SO_3H.0.5H_2O$ | $C_{19}H_{36}N_6O_{14}S_4.0.5H_2O$ | 11.85 | 11.87 | 18.05 | 17.99 | 198 |
| Methyl ester.4 $CH_3SO_3H.0.5H_2O$ | $C_{20}H_{40}N_6O_{17}S_5.0.5H_2O$ | 10.43 | 10.49 | 19.88 | 19.86 | 174 |
| Methyl ester.5 $CH_3SO_3H.0.5H_2O$ | $C_{21}H_{44}N_6O_{20}S_6.0.5H_2O$ | 9.32 | 9.29 | 21.31 | 21.35 | 156 |

EXAMPLE 2

The procedure of Example 1 is followed, using absolute ethanol containing 2% of sulphuric acid.

The SAM ethyl ester is obtained of formula: SAM ethyl ester. $2H_2SO_4.0.5H_2O$

U.V. spectrum: At pH 4, absorption maximum at 258 nm with $\epsilon=14,040$, At pH 1, absorption maximum at 256 nm with $\epsilon=13,500$.

NMR spectrum: At 1.25 p.p.m., triplet of the R—$CH_3$ group At 3 p.p.m., singlet of the $S^+$—$CH_3$ group At 4.2 p.p.m., quadruplet of the

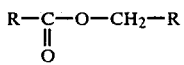

group

When analysed by HPLC under the conditions of Example 1, the product gives a single peak with a retention time of 600 seconds.

As in the case of Example 1, it is possible to obtain an entire series of salts, namely:
SAM ethyl ester. $1.5H_2SO_4.0.5H_2O$
SAM ethyl ester.$2.5H_2SO_4.0.5H_2O$
SAM ethyl ester.$3HCl.0.5H_2O$
SAM ethyl ester.$4HCl.0.5H_2O$
SAM ethyl ester.$5HCl.0.5H_2O$
SAM ethyl ester.$3CH_3SO_3H.0.5H_2O$
SAM ethyl ester.$4CH_3SO_3H.0.5H_2O$
SAM ethyl ester.$5CH_3SO_3H.0.5H_2O$.
All these salts have U.V. and NMR spectra identical to those of the aforesaid salt.

EXAMPLE 3

The procedure of Example 1 is followed, using n-butanol containing 2% of sulphuric acid.

A suspension is initially obtained, which is converted into a clear solution on reflux.

The SAM n-butyl ester is obtained of formula: SAM n-butyl ester.$2H_2SO_4.0.5H_2O$ U.V. spectrum: At pH 4, absorption maximum at 258 nm with $\epsilon=14,040$, At pH 1, absorption maximum at 256 nm with $\epsilon=13,500$.

NMR spectrum: At 0.9 p.p.m., triplet characteristic of the R—$CH_3$ group At 3 p.p.m., singlet of the $S^+$—$CH_3$ group At 4.1 p.p.m., quadruplet characteristic of the

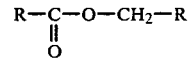

group.

When analysed by HPLC under the conditions of Example 1, the product gives a single peak with a retention time of 650 seconds.

The whole series of salts of Examples 1 and 2 was obtained under the same conditions as described.

By using n-pentanol and n-hexanol instead of butanol, the SAM n-pentyl and n-hexyl esters were obtained.

The following table gives the analytical data for the SAM esters of Examples 2 and 3.

| COMPOUND | EMPIRICAL FORMULA | % N calc. | % N found | % S calc. | % S found | $E_{1\% \ 1 \ cm}$ pH = 4 |
| --- | --- | --- | --- | --- | --- | --- |
| SAM ethyl ester.$2H_2SO_4.0.5H_2O$ | $C_{17}H_{30}N_6O_{13}S_3.0.5H_2O$ | 13.29 | 13.27 | 15.19 | 15.18 | 222 |
| SAM n-propyl ester.$2H_2SO_4.0.5H_2O$ | $C_{18}H_{32}N_6O_{13}S_3.0.5H_2O$ | 13.00 | 13.02 | 14.86 | 14.85 | 217 |
| SAM n-butyl ester.$2H_2SO_4.0.5H_2O$ | $C_{19}H_{34}N_6O_{13}S_3.0.5H_2O$ | 12.73 | 12.71 | 14.55 | 14.52 | 213 |
| SAM n-pentyl ester.$2H_2SO_4.0.5H_2O$ | $C_{20}H_{36}N_6O_{13}S_3.0.5H_2O$ | 12.46 | 12.45 | 14.24 | 14.25 | 208 |
| SAM n-hexyl ester.$2H_2SO_4.0.5H_2O$ | $C_{21}H_{38}N_6O_{13}S_3.0.5H_2O$ | 12.21 | 12.23 | 13.95 | 13.93 | 204 |

EXAMPLE 4

A quantity of SAM sulphate equal to 1 kg of SAM ions is dissolved in 10 l of $H_2O$ and cooled to 1° C.

The pH is adjusted to 7 with 2N NaOH while maintaining this temperature constant by circulating a cooling liquid.

Still maintaining the temperature at 1° C., 285 ml of acetic anhydride are added over a period of 1 hour while at the same time maintaining the pH at 7 by adding 2N NaOH.

After the acetic anhydride addition, the pH is allowed to stabilise under the same temperature conditions, after which the temperature is allowed to rise to 20° C. The conversion yield to the monoacetyl derivative is 95%. The reaction mixture is diluted with 20 l of distilled water.

A column of 50 l of AMBERLITE IRC 50 resin in $H^+$ form, previously activated with 100 l of 0.5N $H_2SO_4$ and washed until neutral, is prepared separately.

The reaction mixture is passed through this column at a rate of 50 l/h.

It is washed with 50 l of distilled water. A 0.1N acetic acid solution (about 400 l) is passed through the column until the pH of the eluate is 3. The column is washed with 50 l of 20 mN $H_2SO_4$ to elute the last traces of unreacted SAM. It is then eluted with 50 l of 0.1N $H_2SO_4$. The solution is concentrated under vacuum (30 mm Hg, 35° C.) to about 10 l. It is treated with 50 g of activated charcoal and filtered.

The solution is titrated, and sufficient concentrated sulphuric acid is added to obtain a molar SAM monoacetyl/$H_2SO_4$ ratio of 1:2, after which it is lyophilised.

900 g of the salt SAM monoacetyl. $2H_2SO_4.0.5H_2O$ are obtained, of composition:
SAM monoacetyl: 68.3%
$H_2SO_4$: 30.3%
$H_2O$: 1.4%
equal to a yield of 61.5% with respect to the SAM.

When analysed by HPLC (PARTISIL 10 SCX column, eluent 0.1M ammonium formate pH 4, 20% methanol, flow 1 ml/min) the product thus obtained gives a single peak with a retention time of 360 seconds.

The product was identified by U.V. and NMR spectra.

U.V. spectrum: at pH 4, absorption maximum at 258 nm with $\epsilon = 14{,}040$, at pH 1, absorption maximum at 256 nm with $\epsilon = 13{,}500$.

NMR spectrum: at 2 p.p.m., singlet of the acetyl group, at 3 p.p.m., singlet of the $S^+$—$CH_3$ group.

The product does not give a positive response to the ninhydrin test, indicating modification of the amino-acid group.

On adjusting the molar stoichiometric ratio to 1.5 or 2.5 with respect to the sulphuric acid before lyophilisation, the following salts were obtained:
SAM monoacetyl.$1.5H_2SO_4.0.5H_2O$
SAM monoacetyl.$2.5H_2SO_4.0.5H_2O$ On using hydrochloric acid or methanesulphonic acid instead of sulphuric acid for the column elution, the following salts were obtained:
SAM monoacetyl.$3HCl.0.5H_2O$
SAM monoacetyl.$4HCl.0.5H_2O$
SAM monoacetyl.$5HCl.0.5H_2O$
SAM monoacetyl.$3CH_3SO_3H.0.5H_2O$
SAM monoacetyl.$4CH_3SO_3H.0.5H_2O$
SAM monoacetyl.$5CH_3SO_3H.0.5H_2O$.

All these salts have the same U.V. and NMR characteristics as the aforesaid product.

The analytical data relative to these salts are given in the following table:

| COMPOUND | EMPIRICAL FORMULA | % N calc. | % N found | % S calc. | % S found | $E_{1\%\ 1\ cm}$ pH = 4 |
|---|---|---|---|---|---|---|
| SAM monoacetyl.$1.5H_2SO_4.0.5H_2O$ | $C_{17}H_{27}N_6O_{12}S_{2.5}.0.5H_2O$ | 14.07 | 14.09 | 13.40 | 13.49 | 235 |
| SAM monoacetyl.$2H_2SO_4.0.5H_2O$ | $C_{17}H_{28}N_6O_{14}S_3.0.5H_2O$ | 13.00 | 12.96 | 14.86 | 14.79 | 217 |
| SAM monoacetyl.$2.5H_2SO_4.0.5H_2O$ | $C_{17}H_{29}N_6O_{18}S_{3.5}.0.5H_2O$ | 12.09 | 12.03 | 16.11 | 16.10 | 202 |
| SAM monoacetyl.$3HCl.0.5H_2O$ | $C_{17}H_{27}N_6O_6SCl_3.0.5H_2O$ | 17.25 | 17.32 | 6.57 | 6.61 | 288 |
| SAM monoacetyl.$4HCl.0.5H_2O$ | $C_{17}H_{28}N_6O_6SCl_4.0.5H_2O$ | 16.06 | 16.04 | 6.12 | 6.09 | 269 |
| SAM monoacetyl.$5HCl.0.5H_2O$ | $C_{17}H_{29}N_6O_6SCl_5.0.5H_2O$ | 15.03 | 15.02 | 5.72 | 5.70 | 251 |
| SAM monoacetyl.$3CH_3SO_3H.0.5H_2O$ | $C_{20}H_{36}N_6O_{15}S_4.0.5H_2O$ | 11.38 | 11.35 | 17.34 | 17.31 | 190 |
| SAM monoacetyl.$4CH_3SO_3H.0.5H_2O$ | $C_{21}H_{40}N_6O_{18}S_5.0.5H_2O$ | 10.07 | 10.09 | 19.18 | 19.16 | 168 |
| SAM monoacetyl.$CH_3SO_3H.0.5H_2O$ | $C_{22}H_{44}N_6O_{21}S_6.0.5H_2O$ | 9.03 | 9.01 | 20.65 | 20.64 | 151 |

EXAMPLE 5

The procedure of Example 4 was followed, but using propionic anhydride, butyric anhydride, hexanoyl chloride, benzoyl chloride, paratoluenesulphonyl chloride, succinic anhydride and glutaric anhydride instead of acetic anhydride. The corresponding SAM acyl derivatives were obtained, of which the analytical characteristics are given in the following table.

| COMPOUND | EMPIRICAL FORMULA | % N calc. | % N found | % S calc. | % S found | $E_{1\%\ 1\ cm}$ pH = 4 |
|---|---|---|---|---|---|---|
| SAM propionyl.$2H_2SO_4.0.5H_2O$ | $C_{18}H_{30}N_6O_{14}S_3.0.5H_2O$ | 12.73 | 12.70 | 14.55 | 14.51 | 213 |
| SAM butyryl.$2H_2SO_4.0.5H_2O$ | $C_{19}H_{32}N_6O_{14}S_3.0.5H_2O$ | 12.46 | 12.48 | 14.24 | 14.24 | 208 |
| SAM hexanoyl.$2H_2SO_4.0.5H_2O$ | $C_{21}H_{36}N_6O_{14}S_3.0.5H_2O$ | 11.97 | 11.95 | 13.68 | 13.70 | 200 |
| SAM benzoyl.$2H_2SO_4.0.5H_2O$ | $C_{22}H_{30}N_6O_{14}S_3.0.5H_2O$ | 11.86 | 11.85 | 13.56 | 13.59 | 198 |
| SAM p-toluenesulphonyl.$2H_2SO_4.0.5H_2O$ | $C_{22}H_{32}N_6O_{15}S_4.0.5H_2O$ | 11.08 | 11.10 | 16.88 | 16.85 | 185 |
| SAM succinyl.$2H_2SO_4.0.5H_2O$ | $C_{19}H_{30}N_6O_{16}S_3.0.5H_2O$ | 11.93 | 11.95 | 13.64 | 13.61 | 199 |
| SAM glutaryl.$2H_2SO_4.0.5H_2O$ | $C_{20}H_{32}N_6O_{16}S_3.0.5H_2O$ | 11.70 | 11.67 | 13.37 | 13.35 | 196 |

EXAMPLE 6

The procedure of Example 4 was followed, but using 1540 ml of decanoyl chloride in about 15 l of acetone instead of the acetic anhydride.

On termination of the reaction, the solution was diluted with 20 l of $H_2O$, the acetone was evaporated under vacuum and the decanoic acid precipitate filtered off.

Proceeding as described in Example 4, the salt SAM decanoyl. $2H_2SO_4.0.5H_2O$ was obtained.

When analysed by HPLC under the conditions of Example 4, the product shows a single peak with a retention time of 340 seconds.

The product also has the following U.V. characteristics: at pH 4, absorption maximum at 258 nm with ε14,040, at pH 1, absorption maximum at 256 nm with ε13,500.

On using octyl chloride and dodecyl chloride instead of the decanoyl chloride, the following products were obtained:
SAM n-octyl.2H$_2$SO$_4$.0.5H$_2$O
SAM n-dodecyl.2H$_2$SO$_4$.0.5H$_2$O
The analytical data for these products are given in the following table.

| COMPOUND | EMPIRICAL FORMULA | % N calc. | % N found | % S calc. | % S found | E$_{1\%\ 1\ cm}$ pH = 4 |
|---|---|---|---|---|---|---|
| SAM n-octyl.2H$_2$SO$_4$.0.5H$_2$O | C$_{23}$H$_{40}$N$_6$O$_{14}$S$_3$.0.5H$_2$O | 11.51 | 11.48 | 13.15 | 13.14 | 192 |
| SAM n-decyl.2H$_2$SO$_4$.0.5H$_2$O | C$_{25}$H$_{44}$N$_6$O$_{14}$S$_3$.0.5H$_2$O | 11.08 | 11.10 | 12.66 | 12.64 | 185 |
| SAM n-dodecyl.2H$_2$SO$_4$.0.5H$_2$O | C$_{27}$H$_{48}$N$_6$O$_{14}$S$_3$.0.5H$_2$O | 10.69 | 10.66 | 12.21 | 12.19 | 179 |

EXAMPLE 7

A quantity of any SAM salt equivalent to 1 kg of SAM ions is dissolved in 10 l of H$_2$O and cooled to 1° C.

The pH is adjusted to 7 with 2N NaOH while maintaining this temperature constant by circulating a cooling liquid.

While maintaining the temperature at 1° C., 1200 ml of acetic anhydride are slowly added over a period of 2 hours, while keeping the pH at 7 by adding 2N NaOH.

The conversion yield to the triacetyl derivative is 80%.

From this point onwards the procedure of Example 4 is followed.

720 g of the salt SAM triacetyl. 2H$_2$SO$_4$.0.5H$_2$O are obtained, of composition:
SAM triacetyl: 71.9%
H$_2$SO$_4$: 26.8%
H$_2$O: 1.3%
equal to a yield of 51.8% with respect to the SAM.

When analysed by HPLC under the conditions of Example 4, the product shows a single peak with a retention time of 820 seconds.

The product also shows the following U.V. and NMR characteristics.

U.V. spectrum: at pH 4, absorption maximum at 258 nm with ε=14,050, at pH 1, absorption maximum at 256 nm with ε=13,500.

NMR spectrum: at 2 p.p.m., singlet of the acetyl on methionine, at 2.2 p.p.m., singlet corresponding to the 2 acetyls on ribose, at 3 p.p.m., singlet of the $$S-CH_3$$
$$+$$

group.

If propionic anhydride or butyric anhydride is used instead of the acetic anhydride, the following products are obtained:
SAM tripropionyl. 2H$_2$SO$_4$.0.5H$_2$O
SAM tributyryl. 2H$_2$SO$_4$.0.5H$_2$O The analytical data for the SAM triacetyl derivatives are given in the following table.

| COMPOUND | EMPIRICAL FORMULA | % N calc. | % N found | % S calc. | % S found | E$_{1\%\ 1\ cm}$ pH = 4 |
|---|---|---|---|---|---|---|
| 2SAM triacetyl.2H$_2$SO$_4$.0.5H$_2$O | C$_{21}$H$_{32}$N$_6$O$_{16}$S$_3$.0.5H$_2$O | 11.51 | 11.50 | 13.15 | 13.12 | 192 |
| SAM tripropionyl.2H$_2$SO$_4$.0.5H$_2$O | C$_{24}$H$_{38}$N$_6$O$_{16}$S$_3$.0.5H$_2$O | 10.88 | 10.85 | 12.43 | 12.40 | 180 |
| SAM tributyryl.2H$_2$SO$_4$.0.5H$_2$O | C$_{27}$H$_{44}$N$_6$O$_{16}$S$_3$.0.5H$_2$O | 10.32 | 10.33 | 11.79 | 11.77 | 172 |

EXAMPLE 8

The procedure of Example 5 is followed, to give reaction mixtures containing SAM hexanoyl, SAM benzoyl and SAM succinyl respectively.

At this point, while maintaining the temperature at 1° C., 1000 ml of acetic anhydride are added over a time of 1 hour while keeping the pH at 7 by adding 2N NaOH. The subsequent procedure then follows Example 4.

The following triacyl derivatives of mixed type are obtained:
SAM hexanoyl-diacetyl.2H$_2$SO$_4$.0.5H$_2$O
SAM benzoyl-diacetyl.2H$_2$SO$_4$.0.5H$_2$O
SAM succinyl-diacetyl.2H$_2$SO$_4$.0.5H$_2$O
for which the analytical data are given in the following table:

| COMPOUND | EMPIRICAL FORMULA | % N calc. | % N found | % S calc. | % S found | E$_{1\%\ 1\ cm}$ pH = 4 |
|---|---|---|---|---|---|---|
| SAM hexanoyl-diacetyl.2H$_2$SO$_4$.0.5H$_2$O | C$_{25}$H$_{40}$N$_6$O$_{16}$S$_3$.0.5H$_2$O | 10.69 | 10.68 | 12.21 | 12.19 | 179 |
| SAM benzoyl-diacetyl.2H$_2$SO$_4$.0.5H$_2$O | C$_{26}$H$_{34}$N$_6$O$_{16}$S$_3$.0.5H$_2$O | 10.61 | 10.60 | 12.12 | 12.10 | 177 |
| SAM succinyl-diacetyl.2H$_2$SO$_4$.0.5H$_2$O | C$_{23}$H$_{34}$N$_6$O$_{18}$S$_3$.0.5H$_2$O | 10.66 | 10.63 | 12.18 | 12.20 | 178 |

All the derivatives of the present invention were tested in a wide pharmacological screening trial, and in all cases showed highly interesting activity and toxicity characteristics.

It was established that the activity of the new compounds depends substantially on their capacity to release the SAM+ ion in the organism, and the capacity of this latter to act as a donor of methyl groups, as the natural substrate of a large number of transmethylase enzymes which catalyse fundamental reactions of the lipid, protide and glucide metabolism.

The importance of the new compounds thus derives substantially from the fact that they make the S-adenosylmethionine absolutely stable, so enabling its transmethylating activity in the human organism to be utilised 100% without the risk of formation of toxic degradation products which interfere negatively with the biological processes activated by the SAM+.

It also depends on their capacity to cause the SAM to pass through the cell barriers, and thus to make it highly bioavailable.

TOXICITY

The acute toxicity in the mouse was determined, the following values being obtained in all cases:
$LD_{50}$ by oral administration $>3$ g/kg
$LD_{50}$ by intravenous administration $>1$ g/kg.

Tolerability and chronic toxicity tests were carried out on rats of the Wistar and Sprague-Dowley stock, by administering 20 mg/kg per day of product for 12 months. On termination of the treatment, the various organs and systems showed no pathological alteration.

Teratogenesis tests were carried out on rabbits. When salt doses ten times greater than the maximum therapeutic doses were administered, no teratogenic action or malformative action on the embryos or terminal fetuses was encountered.

Intravenous administration of doses up to 200 mg/kg caused no pyrogenic manifestation in the rabbit.

Venous administration of 40 mg/kg in the rabbit and rat caused no change in carotid pressure, cardiac and respiratory frequency, or in the electrocardiograph trace.

Local tolerability of intramuscular injection, even after administrations repeated for 30-60 days, and of intravenous injection in the marginal vein of the outer ear of the rabbit, was excellent.

PHARMACOLOGY

An entire series of tests carried out on rats have shown that the new products exert a very considerable protective and resolving action in hepatic steatosis induced by a hyperlipid-hyperprotein diet in accordance with Handler, and in steatosis induced by acute alcoholic intoxication and other toxic agents even when administering doses of 10 mg/kg of SAM+.

In experimental hyperlipemia in the rat, for example induced by Triton S, the new products have demonstrated a very conspicuous hypolipemic activity which, in relation to the dose used, i.e. 10 mg/kg (again expressed in SAM+), was much more intense than in the case of other drugs of hypolipemic activity.

In chickens rendered atherosclerotic by means of diets enriched in cholesterol and fructose, parenteral administration of the new products in doses of 10 mg/kg reduced the cholesterolemia and favourably modified lesions encountered in the controls with respect to the thoracic and abdominal aorta and the small vessels of the encephalic base.

With regard to phospholipid metabolism, it was found experimentally that there was an increase in the phosphatidylcholine quantity in the hepatic tissue of rats with uncompensated steatosis. A clear increment in the phosphatidylcholine was also determined at the expense of the hematic $\alpha$-lipoproteins in experimental alterations caused by $\beta/\alpha$ lipoprotein ratios.

All these tests have clearly indicated a curative effect of the new derivatives in alterations of the lipid metabolism.

A further series of tests carried out on the rat have shown that administration of 1 mg/kg doses induces an accumulation of glycogenic reserves at the hepatic and muscular level, which is demonstrated both by histochemical methods and by quantitative determinations. In experimental diabetes induced by alloxan, the insulin quantity necessary for returning glycemia values to normal was considerably reduced by administrations equivalent to 0.5 mg/kg of SAM+.

This series of tests has demonstrated a clear positive action of the new compounds according to the invention on the glucide metabolism.

Finally, rats with experimentally induced hypodisproteinemia were treated with quantities of 10 mg/kg of SAM derivatives. It was found that said products return the total proteinemia values to normal, by substantially increasing the albumin level and thus showing marked protein anabolic activity.

This and other similar tests have demonstrated the curative power of the new products in malfunctions of the protide metabolism.

Summarising, on the basis of the aforesaid briefly described pharmacological tests and of many others which have enabled the activity of the new products to be explored at all levels in the human organism, the activity of the new products has been clinically established in hepatology in the case of acute and chronic hepatic intoxication, in neurology as an antidepressive, and in osteology in the case of rheumatoid arthritis.

The activity in numerous other fields of human therapy is under investigation.

The new products have also quite unexpectedly shown considerable anti-inflammatory and analgesic activity.

The new products can be administered orally, or by intramuscular or intravenous injection. However, as they are characterised by greater intestinal absorption than SAM, they are particularly useful for the preparation of pharmaceutical formulations for oral use.

Other possible administration forms are suppositories, liquids for ocular installation, aerosol, or forms for topical application.

I claim:

1. S-adenosylmethionine (SAM) derivatives of formula:

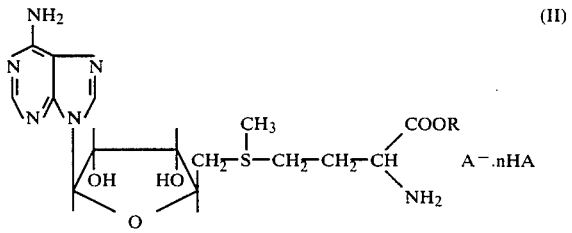

in which R is a linear or branched aliphatic radical containing 1 to 6 carbon atoms, A is an equivalent of a generic anion of a strong inorganic or organic acid of pK<2.5 and n can vary from 0 to 4.

2. S-adenosylmethionine (SAM) derivatives of formula:

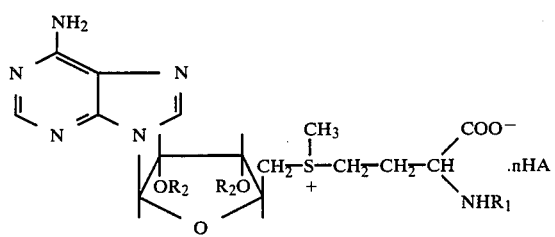

(III)

in which $R_1$ and $R_2$, which can be the same or different, are a linear or branched aromatic or aliphatic acyl containing 2 to 12 carbon atoms; A is an equivalent of an inorganic or organic acid of pK<2.5, and n can vary from 1 to 5.

3. A process for preparing S-adenosylmethionine esters of formula:

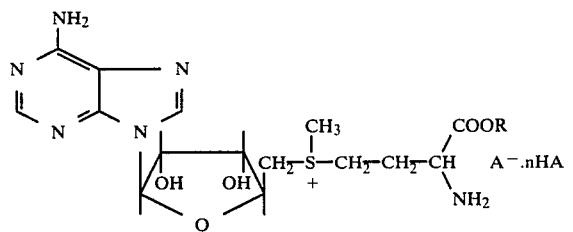

in which R is a linear or branched aliphatic radical of 1 to 6 carbon atoms, A is an equivalent of a generic anion of a strong inorganic or organic acid of pK<2.5, and n is 0-4, characterised in that a solution of a SAM salt in the required alcohol containing 1-3% of $H_2SO_4$ is heated under reflux, and the ester formed is purified by passing an aqueous solution thereof through a column of weak acid resin, eluting with a dilute aqueous solution of the required acid, and adding, to the aqueous solution obtained after concentration, the stoichiometric quantity of acid necessary for the chosen value of n.

4. A process for preparing S-adenosylmethionine derivatives of formula:

in which $R_1$ and $R_2$, which can be the same or different, are a linear or branched aliphatic or aromatic acyl containing 2 to 12 carbon atoms; A is an equivalent of an inorganic or organic acid of pK<2.5, and n=1-5, characterised in that an aqueous solution of a SAM salt is treated with an acylating agent selected from the group consisting of anhydride and chloride of carboxylic acid, at a temperature of about 1° C. and pH 7, on termination of the reaction the solution is passed through a weak acid resin which is eluted with an aqueous solution of the required acid, and the stoichiometric quantity of acid necessary for the chosen value of n is added to the solution obtained after concentration.

5. A process as claimed in claim 4, wherein the $C_7$-$C_{12}$ monoacyl derivatives are obtained by using an excess of the acid chloride in an acetone solution.

6. A process as claimed in claim 4, wherein the $C_2$-$C_6$ triacyl derivatives are obtained by using a strong excess of the acid anhydride or chloride.

7. A composition for the treatment of hyperlipemia comprising an antihyperlipemic effective amount of the compound of claim 1 and a therapeutically acceptable carrier.

8. A composition for the treatment of hyperlipemia comprising an antihyperlipemic effective amount of the compound of claim 2 in a therapeutically acceptable carrier.

9. The S-adenosylmethionine derivative of claim 1, wherein n is 3.

10. The S-adenosylmethionine derivative of claim 2, wherein n is 4.

* * * * *